United States Patent
Bolmsjö et al.

(10) Patent No.: US 8,518,016 B2
(45) Date of Patent: *Aug. 27, 2013

(54) METHOD OF USING A PARTIAL-LENGTH, INDWELLING PROSTATIC CATHETER HAVING A COILED INFLATION TUBE AS AN ANCHOR

(75) Inventors: Magnus Bolmsjö, Lund (SE); Sonny Schelin, Rockneby (SE)

(73) Assignee: ProstaLund AB, Lund (SE)

( * ) Notice: Subject to any disclaimer, the term of this patent is extended or adjusted under 35 U.S.C. 154(b) by 395 days.

This patent is subject to a terminal disclaimer.

(21) Appl. No.: 12/818,572

(22) Filed: Jun. 18, 2010

(65) Prior Publication Data

US 2010/0256608 A1   Oct. 7, 2010

Related U.S. Application Data

(62) Division of application No. 10/665,742, filed on Sep. 17, 2003, now Pat. No. 7,766,899.

(51) Int. Cl.
*A61M 1/00* (2006.01)
*A61M 27/00* (2006.01)
*A61M 5/00* (2006.01)
*A61M 31/00* (2006.01)
*A61F 2/04* (2013.01)

(52) U.S. Cl.
USPC .......... 604/540; 604/544; 604/8; 604/9; 604/96.01; 606/108; 606/191; 623/23.64; 623/23.65; 623/23.66; 623/26

(58) Field of Classification Search
USPC ............. 604/540, 544, 93.01, 95.03, 96.01, 604/101.03, 101.04, 103, 103.11
See application file for complete search history.

(56) References Cited

U.S. PATENT DOCUMENTS

| | | | | |
|---|---|---|---|---|
| 5,300,022 | A | * | 4/1994 | Klapper et al. ............ 604/35 |
| 5,322,501 | A | * | 6/1994 | Mahmud-Durrani ......... 604/8 |
| 5,466,222 | A | * | 11/1995 | Ressemann et al. ... 604/103.09 |
| 5,569,219 | A | * | 10/1996 | Hakki et al. ............. 604/524 |
| 6,290,666 | B1 | * | 9/2001 | Devonec ............... 623/1.16 |
| 6,494,855 | B2 | * | 12/2002 | Rioux et al. ............. 602/67 |
| 7,662,145 | B2 | * | 2/2010 | Bolmsjo et al. .......... 604/544 |
| 7,766,899 | B2 | * | 8/2010 | Bolmsjo et al. .......... 604/540 |
| 2002/0072788 | A1 | * | 6/2002 | Hammond et al. ....... 623/1.11 |
| 2003/0078467 | A1 | * | 4/2003 | Whalen et al. ............ 600/30 |
| 2003/0153807 | A1 | * | 8/2003 | Whalen et al. ............ 600/30 |
| 2010/0106142 | A1 | * | 4/2010 | Bolmsjo et al. .......... 604/544 |

* cited by examiner

*Primary Examiner* — Adam Marcetich
(74) *Attorney, Agent, or Firm* — John R. Ley

(57) ABSTRACT

An indwelling catheter is positioned in a urinary tract to drain urine from the bladder to a position distally adjacent to a sphincter muscle. A balloon of the catheter is inflated through an inflation tube extending through the urinary tract. A coiled section of the inflation tube contacts the constriction caused by the sphincter muscle. The balloon and the coiled section resist movement of the indwelling catheter while still permitting natural urination. The indwelling catheter is inserted by an insertion tool which is separably connected to the catheter. Once the indwelling catheter is positioned, the tool is disconnected and withdrawn from the urinary tract. Risks of blood clots obstructing the flow of urine through the indwelling catheter immediately following a surgical procedure on the prostate gland are avoided by flushing fluid through the insertion tool and the catheter to clear an internal urine flow passageway in the catheter.

19 Claims, 9 Drawing Sheets

METHOD OF USING A PARTIAL-LENGTH, INDWELLING PROSTATIC CATHETER HAVING A COILED INFLATION TUBE AS AN ANCHOR

CROSS-REFERENCE TO RELATED APPLICATION

This is a division of U.S. patent application for a Partial-Length Indwelling Prostatic Catheter Using Coiled Inflation Tube as an Anchor and Methods of Draining Urine and Flushing Clots, Ser. No. 10/665,742, filed on Sep. 17, 2003, now U.S. Pat. No. 7,766,899 issued Aug. 3, 2010, which was filed by the inventors hereof and assigned to the assignee hereof.

FIELD OF THE INVENTION

This invention relates to an indwelling urinary catheter and methods of draining urine from a bladder using the indwelling catheter and of flushing an indwelling catheter of obstructions. More particularly, the present invention relates to a new and improved indwelling prostatic urethral catheter using a coiled section of an inflation tube as an anchor against movement of the catheter from its use position, a new and improved method of using such a catheter to permit natural and reliable control over urine flow, and a new and improved method of flushing such a catheter of obstructions caused by blood clots after a surgical procedure.

BACKGROUND OF THE INVENTION

Prostate problems, such as benign prostate hyperplasia (BPH) and malignant prostate cancer, are common occurrences among older men. The effects of these diseases are generally accompanied by swelling or enlargement of the prostate gland. Apart from the life-threatening aspects of malignant prostate cancer, the everyday symptoms and effects of these diseases are usually troublesome. One such problem relates to the ability to control and achieve normal urine discharge. When the prostate gland enlarges to the extent that the prostatic urethra, the part of the urinary tract which extends through the prostate gland, becomes obstructed or restricted, considerable difficulties arise in discharging urine at will. Such difficulties are typically referred to as urinary tract retention. Urinary tract retention can be either acute or chronic.

Surgical treatments are available for relieving urinary tract retention problems. Those treatments include microwave thermotherapy and transurethral resection of the prostate (TURP). Microwave thermotherapy and some other heat treatments involve heating the prostatic urethra and surrounding prostate tissue to such an extent that the tissue is destroyed. Thereafter, the destroyed tissue sloughs off or is absorbed in the body, resulting in an enlargement of the urinary tract through the prostate gland. The enlargement of the urinary tract through the prostate gland eliminates or relieves the obstruction or restriction and permits better urine flow. A TURP procedure involves surgically resecting tissue from the prostate gland to eliminate or reduce obstruction or restriction.

Both thermotherapy and TURP surgical procedures cause temporary side effects, for example inflammation and swelling of the prostate. The side effects usually require the patient to use an indwelling drainage catheter for a few days up to several weeks following the procedure to permit urination while the swelling subsides and the tissue of the prostate gland heals or stabilizes. The tissue of the prostate gland which remains viable after the thermotherapy or TURP procedure is quite raw and tender, and direct contact from urine can aggravate the inflammation and increase the risk of infection. An indwelling catheter permits the urine to pass through the tissue where the surgical procedure was performed with only minimal contact to the treated tissue.

In those cases where the diseased prostate gland cannot be treated with thermotherapy or a TURP procedure, the obstruction or restriction may become so significant that normal urinary functions are not possible or are only possible with great difficulty. In these circumstances, it is necessary for a catheter to be used for the rest of the patient's life. In some cases, the patient is taught to insert a full-length catheter whenever urination is necessary. In other cases where the patient cannot insert a full-length catheter himself, the full-length catheter is inserted in the urinary tract and remains in place until removed by medical personnel.

The typical type of urinary catheter used while the prostate gland heals, or on a continual basis, is a full-length urinary catheter. A full-length urinary catheter extends from the exterior of the patient through the entire length of the urinary tract into the bladder. A clamp or other mechanical valve is attached at the exterior of the full-length urinary catheter, and the clamp is opened to void the urine from the bladder. Sometimes a reservoir is also attached to the end of the full-length catheter to collect the urine discharge. The urinary sphincter muscle, which normally controls the flow of urine from the bladder, is no longer able to perform its natural function of constricting the urethra to control urine flow because the full-length urinary catheter provides a continuously open flow path for the urine. The urinary sphincter muscle is not able to constrict the flow path through the full-length urinary catheter.

In addition to the patient lacking the ability to naturally control urine flow, the existence of the full-length urinary catheter extending out of the urinary tract, and presence of the clamp and the reservoir cause discomfort and are awkward to deal with and embarrassing for the patient. The full-length urinary catheter may create limitations from a social standpoint and almost always creates a variety of quality of life issues which must be confronted. Sexual activity is impossible. An increased risk of infection also results.

Because of the quality of life and social issues associated with full-length urinary catheters, partial-length indwelling catheters have been developed. Partial-length indwelling catheters typically extend only from the bladder through the prostate gland, and not along the entire length of the urinary canal through the penis to the exterior of the body. The reduced length permits the urinary sphincter muscle to control urine flow more naturally, while still bypassing most of the urine flow around the swollen or raw prostate gland. No sizeable part of the catheter extends out of the urinary canal at the penis.

Keeping a partial-length indwelling catheter in the proper position is essential. The short length may allow the catheter to move completely into the bladder or move out of the prostatic urethra into the urinary canal. Either type of unintended movement may require serious medical intervention to correct.

A partial-length urinary catheter typically uses an inflatable balloon at its distal end to prevent the catheter from withdrawing from the bladder and moving out of the prostatic urethra and into the urinary canal. However, the balloon cannot prevent the partial-length urinary catheter from moving into the bladder and thus out of the prostate gland and urethra.

One way of preventing a partial-length urinary catheter from moving into the bladder involves attaching a relatively short and rigid anchor tube to the partial-length catheter with a short length of thread-like material. The anchor tube is approximately as large in diameter as the catheter. The catheter and the anchor tube are positioned in the urinary canal on opposite sides of the urinary sphincter muscle. The thread-like material extends through urethra of the urinary sphincter muscle. The urinary sphincter muscle is able to constrict around the thread-like material to stop urine flow and is able to dilate to permit the flow of urine, in a natural manner. The anchor tube is hollow to pass the discharged urine through the urinary canal. By positioning the anchor tube on the opposite side of the urinary sphincter muscle from the partial-length catheter within the prostatic urethra, the normal constricted state of the urinary sphincter muscle adjacent to the anchor tube prevents the partial-length catheter from moving into the bladder.

Another type of partial-length urinary catheter substitutes a three-dimensionally shaped anchor element for the anchor tube. The anchor element is also connected to the partial length urinary catheter by a tether-like thread. The three-dimensional anchor element is located within the urinary canal proximal of the urinary sphincter muscle, and the tether-like thread extends through the urethra within the urinary sphincter muscle to make natural control over urination possible.

Inserting and removing the rigid tube or three-dimensional anchor element along with the partial-length urinary catheter may be difficult or painful. Special types of insertion tools and techniques are required to use partial-length urinary catheters with rigid tube and three-dimensional anchor elements.

Because the partial-length prostatic urinary catheter must be inserted with the balloon deflated, all such balloon catheters must have some provision for inflating the balloon after the proper position of the catheter is attained. To inflate the balloon, a conduit or channel for adding fluid to the balloon must extend from the balloon to the exterior of the urinary tract. In a related context, the balloon must be deflated to remove the urinary catheter. Typically the balloon is deflated by opening a valve attached to the catheter. Opening the valve allows the fluid to escape from the balloon, so that the catheter can thereafter be removed. Should the valve not open when intended, medical intervention is required to deflate the balloon.

Another difficulty is that the inflated balloon may slowly lose the inflation fluid. Such fluid loss may arise because the valve which confines the fluid to the balloon does not seal completely or because of slight pinhole breaches in the structural materials which form the balloon or seal it to the partial-length prostatic catheter. The risk of fluid loss is exacerbated because of the relatively lengthy time that the partial length urinary catheter remains in use, typically a few weeks. Longer use times provide a greater opportunity for balloon deflation. Any attempt to reinflate a balloon will generally require some form of medical intervention.

These and other considerations and disadvantages of previous indwelling catheters and their use have led to the improvements of the present invention.

SUMMARY OF THE INVENTION

In general, the present invention pertains to a partial-length indwelling prostatic urinary catheter which diverts a substantial majority of the urine flow from the bladder past a prostate gland while still enabling the patient to control urine flow naturally with the urinary sphincter muscle. The retention of the partial length indwelling catheter in its desired location is facilitated, while minimizing the discomfort to the patient and irritation to the urinary tract, by incorporating a coiled section of an inflation tube and a balloon as anchor elements to retain the catheter in a desired use position. The inflation tube extends through the urinary canal to permit a balloon to be inflated as needed. The coiled section of the inflation tube is resilient enough to develop holding force and to constrict when the catheter is withdrawn by pulling on the inflation tube. The partial-length urinary catheter can also be inserted into and removed from the urinary tract in a convenient manner with reduced pain or discomfort. The partial-length urinary catheter may also be inserted immediately after a surgical procedure performed on the prostate gland, and risks of obstructive blood clots in the catheter from blood from the surgically affected prostate gland are diminished by flushing fluid through the insertion tool and the catheter until the risk of blood clots has subsided. The improvements of the present invention also diminish the personal and social issues associated with the use of an indwelling catheter, by minimizing the size and amount of apparatus located exteriorly of the urinary tract at the penis.

In accordance with these and other aspects, the present invention relates to an indwelling catheter which drains urine from a bladder to a position adjacent to a urinary sphincter muscle in a urinary canal extending from the sphincter muscle to an exterior opening. The indwelling catheter includes a main body having a distal end, a proximal end and a length sufficient to position the distal end within the bladder and to position the proximal end distally of the sphincter muscle within the urinary tract. The main body defines a urine drainage channel extending from the distal end to the proximal end. A balloon is attached to the distal end of the main body. The balloon is inflated and expanded to contact the bladder. Upon contact with the bladder, the inflated balloon restrains the main body against proximal movement within the urinary tract from a use position. In the use position, the distal end of the main body is located in the bladder and the proximal end of the main body is distal of the sphincter muscle. A distal end of an inflation tube is connected to the main body. The inflation tube has a length sufficient to extend from the main body through the sphincter muscle and the urinary canal to locate a proximal end of the inflation tube at the exterior opening of the urinary canal. An inflation passageway communicates fluid through the inflation tube to expand the balloon. A coiled section is formed in the inflation tube. The coiled section is located within the urinary canal proximal of the sphincter muscle when the balloon contacts the bladder. The coiled section interacts with the constriction of the urinary tract by the sphincter muscle to restrain the main body against distal movement within the urinary tract from the use position. In this manner the balloon and the coiled section act as anchors to hold the indwelling catheter in the use position. Adequate inflation of the balloon is maintained by adding fluid through the inflation tube if needed. The coiled section resiliently deflects against the urinary canal and the constriction from the sphincter muscle to assist in holding the indwelling catheter in the use position, but the coiled section readily deflects to smaller dimensions when the inflation tube is pulled proximally to remove the indwelling catheter from the urinary tract.

Other aspects of the invention relate to an assembly of the indwelling catheter and an insertion tool. The insertion tool connects to the indwelling catheter to move it within the urinary tract to the use position. The insertion tool has first and second opposite ends and a length sufficient to position the first end within the urinary tract distal of the sphincter muscle while the second end is at the exterior of the urinary canal. The coiled section winds around the insertion tool when the insertion tool is connected to the indwelling catheter. A separable connection is located between the main body and the insertion tool. The separable connection connects the main body to the insertion tool when positioning the indwelling catheter in the use position, and the separable connection disconnects the main body from the insertion tool after the indwelling catheter assumes the use position. Disconnection is achieved preferably in response to proximal movement of the insertion tool after contact of the balloon with the bladder.

The invention also relates to a method of draining urine from the bladder to a position distal of the urinary sphincter muscle in the urinary tract. The method involves positioning an indwelling catheter having an inflatable balloon in the urinary tract in a use position in which the indwelling catheter extends from the bladder to a position distally adjacent to the sphincter muscle. An inflation tube having a coiled section is extended within the urinary tract from the indwelling catheter through the urinary canal through the sphincter muscle and out of the exterior opening of the urinary canal. The balloon is inflated within the bladder by delivering fluid though the inflation tube. The indwelling catheter is retained against proximal movement from the use position by contacting the inflated balloon with the bladder. The indwelling catheter is retained against distal movement by contacting the coiled section with a constriction of the urinary tract caused by the sphincter muscle at a location proximal of the constriction. Urine is then drained through the indwelling catheter. The flow of urine through the urinary canal is controlled by the constriction of the sphincter muscle around the inflation tube.

Additional aspects of the invention involve attaching the indwelling catheter to an insertion tool, inserting the indwelling catheter while connected to the insertion tool into the urinary tract from the exterior opening, manipulating the insertion tool to position the indwelling catheter in the use position, detaching the insertion tool from the indwelling catheter, and withdrawing the insertion tool from the urinary tract. Obstructions within the interior passageway of the indwelling catheter, such as those which result from blood clots after a surgical procedure on the prostate gland, are removed during the time of highest prevalence of such obstructions. Obstructions are removed by flushing the interior passageway of the indwelling catheter with flushing fluid. The insertion tool is maintained connected to the indwelling catheter to permit the delivery of the flushing fluid through the interior channel in the insertion tool. Once the risks of obstructions from blood clots have passed, the insertion tool is disconnected from the indwelling catheter and removed from the urinary tract.

A more complete appreciation of the scope of the present invention and the manner in which it achieves the above-noted and other improvements can be obtained by reference to the following detailed description of presently preferred embodiments taken in connection with the accompanying drawings, which are briefly summarized below, and by reference to the appended claims.

DETAILED DESCRIPTION

Figure 1:
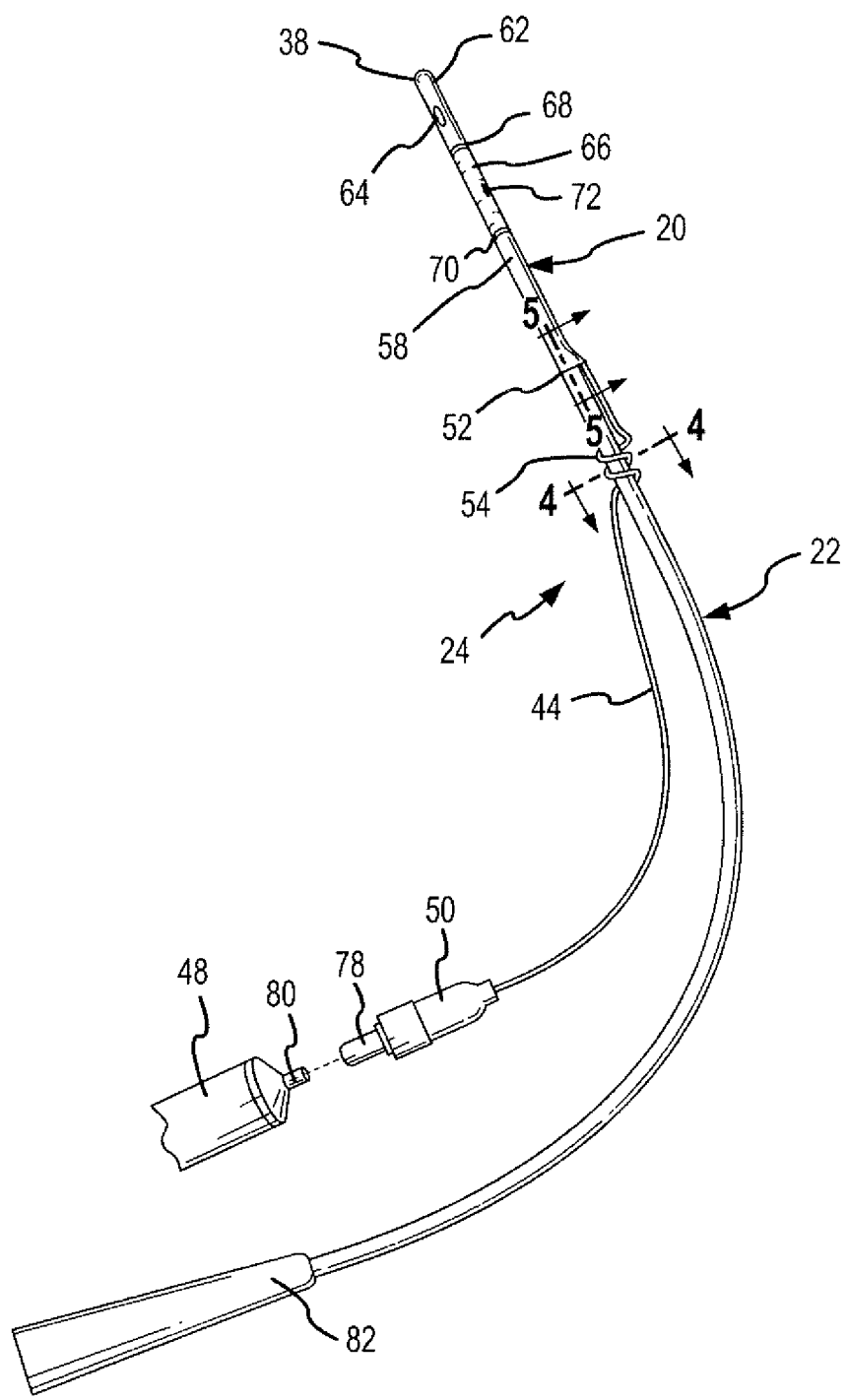
FIG. 1 is a perspective view of an indwelling prostatic catheter which incorporates the present invention, shown attached to an insertion tool and used with a syringe.
Figure 2:
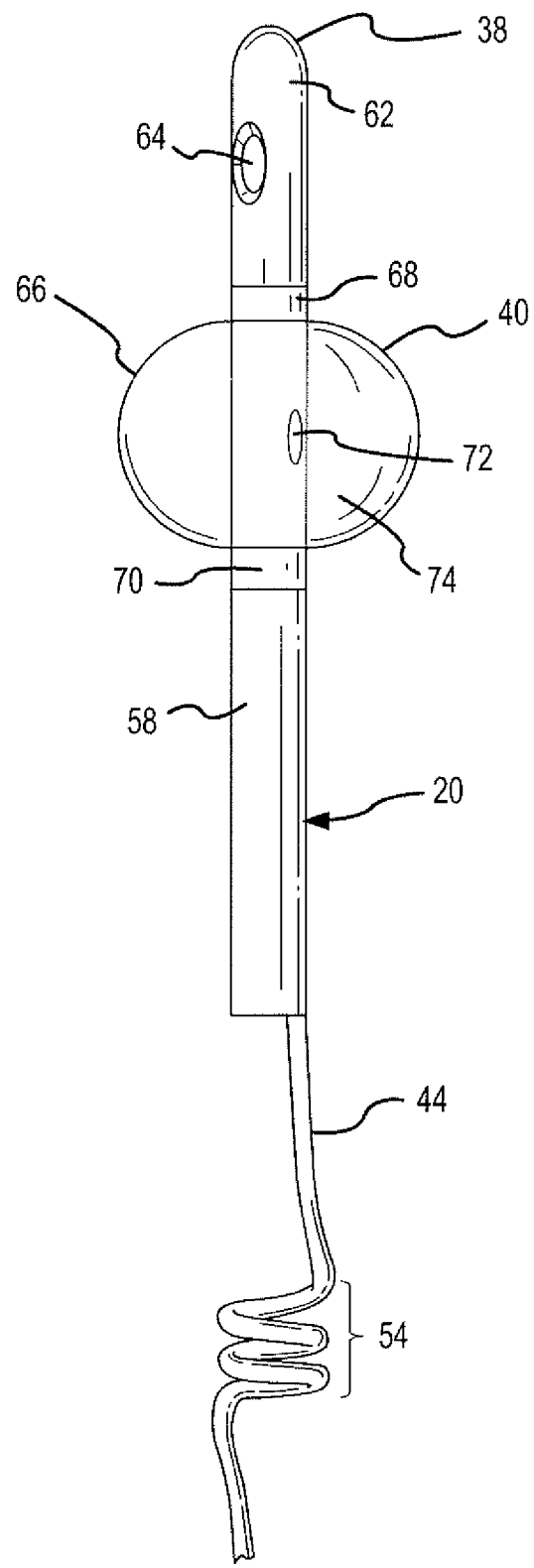
FIG. 2 is an enlarged perspective view of the indwelling prostatic catheter shown in FIG. 1 with the insertion tool removed and with a balloon of the indwelling catheter expanded.
Figure 6:
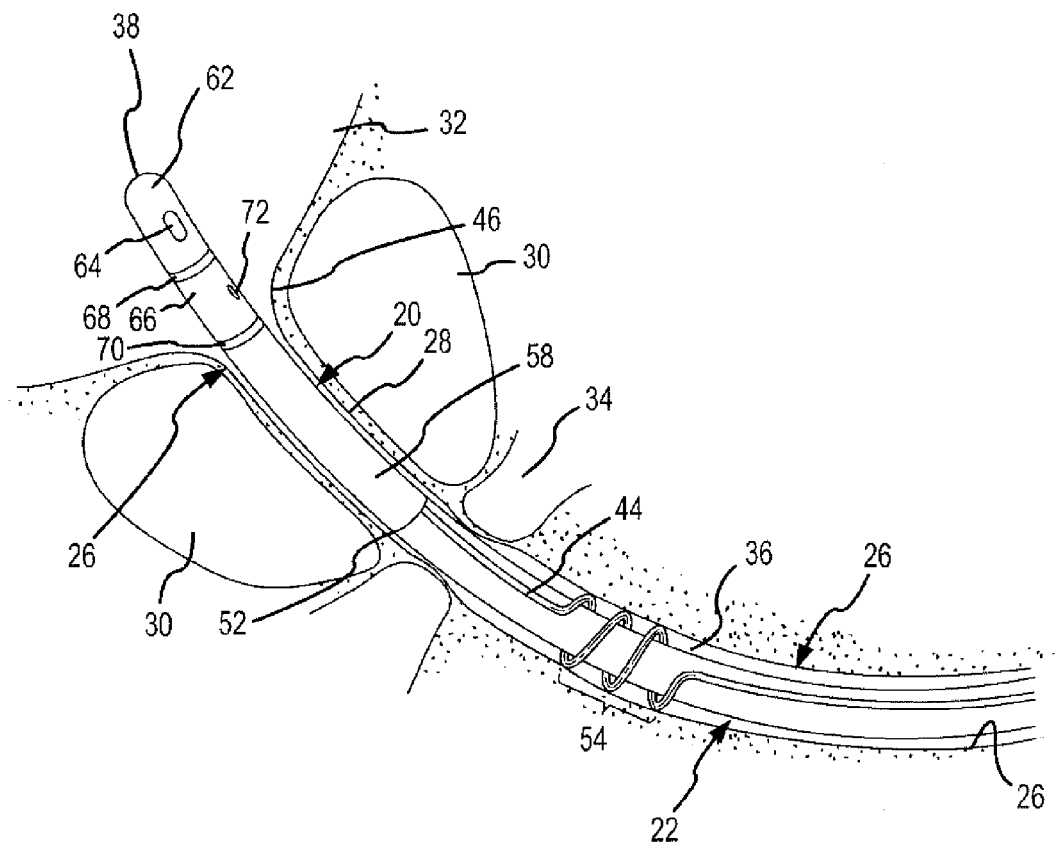
FIG. 6 is a perspective view of the indwelling catheter and a portion of the insertion tool shown in FIG. 1, shown inserted within a urethra, a urethra sphincter, a prostatic urethra and a bladder of a urinary tract of a human being, with the physiology generally illustrated in cross section.

An indwelling catheter 20 which incorporates the present invention is shown in FIG. 1. The indwelling catheter 20 connected to an insertion tool 22, to form a catheter-tool assembly 24 which allows the catheter 20 to be inserted into a urinary tract 26 of a human being, as shown in FIG. 6. Once inserted, the insertion tool 22 is disconnected or separated from the indwelling catheter 20 to leave the catheter 20 dwelling or remaining within a prostatic urethra 28 within a prostate gland 30, as shown in FIG. 9. In its indwelling use position shown in FIGS. 8 and 9, the catheter 20 drains urine from a bladder 32 through the prostatic urethra 28 within the prostate gland 30 to a position distal of a urinary sphincter muscle 34. When the urinary sphincter muscle dilates, the urine drains out into and through an external urinary canal 36 of the urinary tract 26.

The catheter 20 will typically be left in the indwelling position shown in FIG. 9 for a number of days or weeks to function as a temporary stent to protect raw tissue after the prostate gland 30 has been operated on to remove portions of the prostatic urethra 28 and surrounding tissue of the prostate gland 30 in a transurethral resection of the prostate (TURP) surgical procedure, or after these tissues have been destroyed by a microwave or other thermotherapy treatment. In addition, the catheter 20 can also be used as a stent through the prostatic urethra 28 when it has been constricted to the point where urine will no longer pass effectively as a result of swelling in the prostate gland 30 due to benign prostate hyperplasia (BPH) or other abnormalities. There are other reasons to use the indwelling catheter 20.

Figure 7:
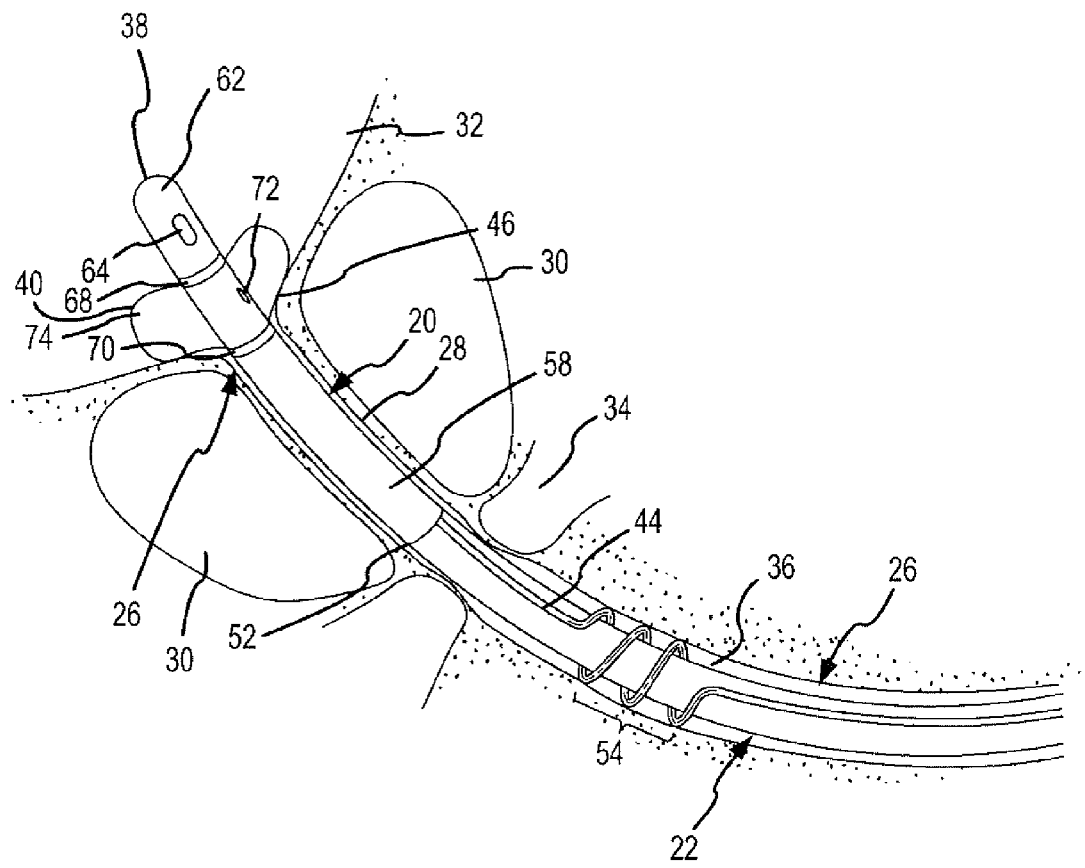
FIG. 7 is an illustration similar to FIG. 6 showing the balloon inflated within the bladder.

The indwelling catheter 20 is positioned as shown in FIG. 9 by pushing the catheter 20 up the urinary canal 36 into the urinary tract 26 with the insertion tool 22 until a distal end 38 of the indwelling catheter 20 enters the bladder 32 as shown in FIG. 6. A balloon 40 on the indwelling catheter 20 is inflated with fluid conducted through an inflation passageway 42 of an inflation tube 44 (FIG. 3) until the balloon 40 is larger in diameter than a neck 46 of the bladder 32 surrounding the prostatic urethra 28. The inflation fluid may be gas, such as air, or liquid such as saline solution. The balloon 40 is preferably inflated from an inflation pump such as a syringe 48 which is connected to a valve assembly 50 at the end of the inflation tube 44 (FIG. 1). Once the balloon 40 has been inflated, the insertion tool 22 is pulled proximally until the inflated balloon 40 is seated on the bladder neck 46, as shown in FIG. 7. When seated on the bladder neck 46, the balloon 40 prevents the indwelling catheter 20 from moving further in the urinary canal in a proximal direction.

Figure 8:
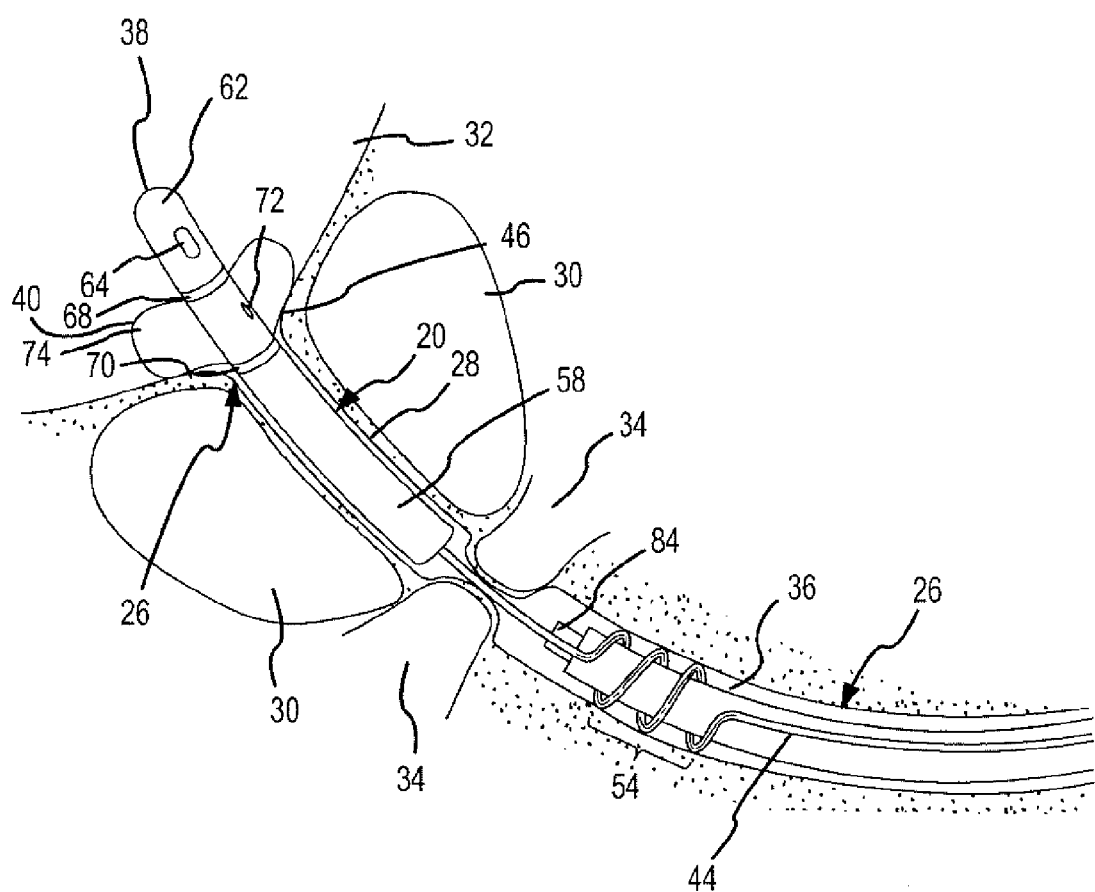
FIG. 8 is an illustration similar to FIGS. 6 and 7 showing separation of the insertion tool from the indwelling catheter.
Figure 9:
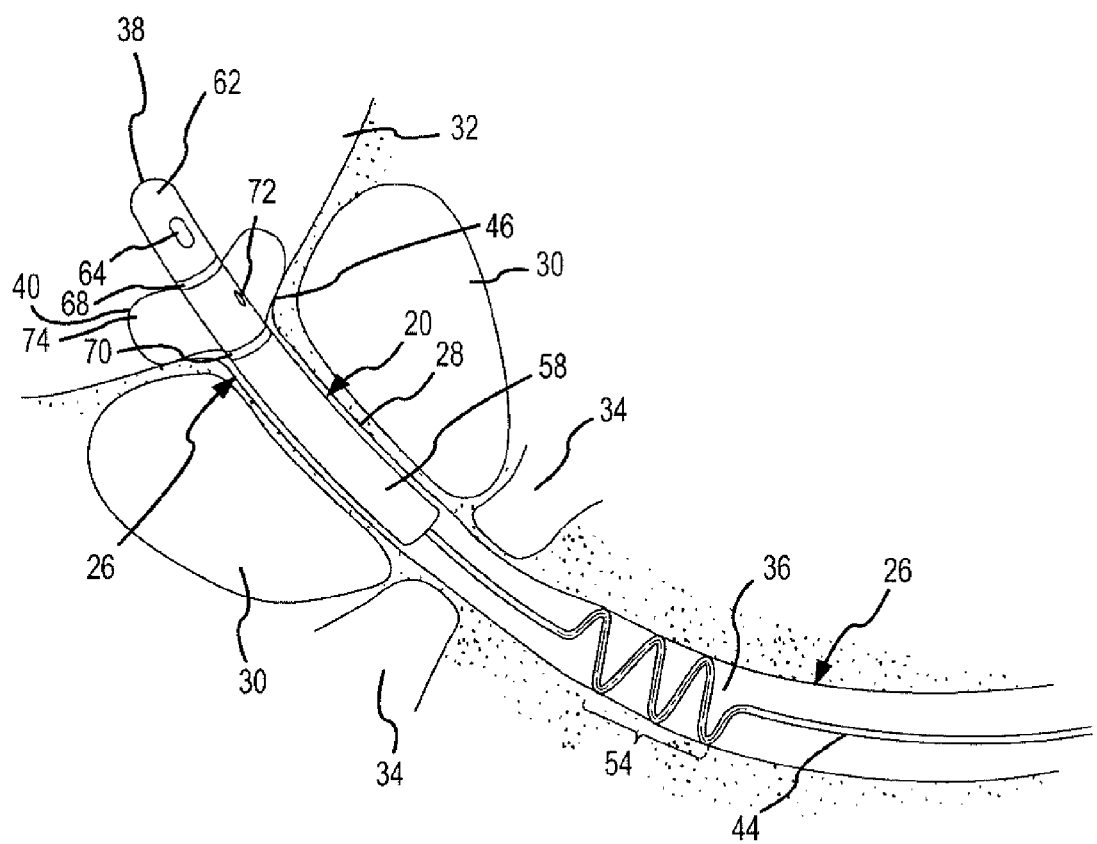
FIG. 9 is an illustration similar to FIGS. 6-8 showing the position and use of the indwelling catheter.

Continued proximal movement of the insertion tool 22 causes it to separate from the catheter 20 at a separable connection 52 (FIG. 1) between the indwelling catheter 20 and the insertion tool 22 as shown in FIG. 8, thereby leaving the indwelling catheter 20 in its final, indwelling position shown in FIG. 9. The insertion tool 22 is thereafter removed from the external urinary canal 36 by withdrawing it in the proximal direction. The inflation tube 44 remains within the urinary canal 36.

The inflation tube 44 is formed with a permanently helically coiled section 54 shown in FIGS. 1-3 and 6-9. The coiled section 54 is resilient both in the transverse dimension and in the longitudinal dimension. The inflation tube 44 has sufficient strength to maintain the coiled section 54 in the coiled configuration within the urinary canal 36 after removal of the insertion tool 22. Because of the resiliency of the coiled section 54, the coiled section 54 presses against the interior of the urinary canal 36. In this way the coiled section 54 resists movement along the urinary canal 36 to hold the indwelling catheter 20 from moving along the urinary canal 36. By resiliently pressing against the interior of the urinary canal 36, the coiled section 54 also minimizes discomfort to the patient or irritation to the urinary canal 36. The coiled section 54 is not disruptive to the flow of urine through the urinary canal 36 because the coiled section 54 provides a fluid-flow path through an open center of the coils.

Figure 4:
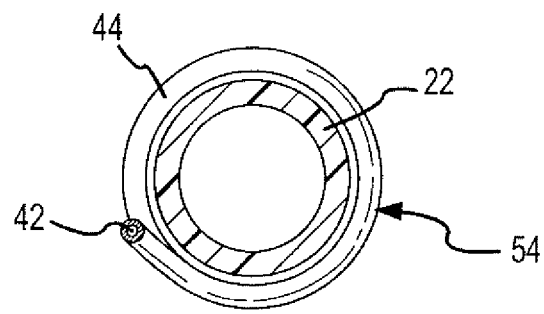
FIG. 4 is an enlarged transverse cross section view taken substantially in the plane of line 4-4 of FIG. 1.

With the catheter 20 connected to the insertion tool 22, the coiled section 54 extends around the exterior of the insertion tool 22, as shown in FIG. 4. By extending around the exterior of the insertion tool 22, the coiled section 54 assists in holding the inflation tube 44 adjacent to the insertion tool 22 while the indwelling catheter 20 and the insertion tool 22 are inserted in the urinary tract 26. The coiled section 54 therefore assists in moving the inflation tube 44 into the urinary tract 26 along with the insertion tool 22. The helically coiled section 54 is loosely wound around the insertion tool 22, thereby allowing the insertion tool 22 to be withdrawn through the center of the coiled section 54 as the insertion tool 22 is disconnected from the indwelling catheter 20.

The coiled section 54 is located a short distance proximally from the proximal end of the indwelling catheter 20. The length of the inflation tube 44 between the proximal end of the indwelling catheter 20 and the coiled section 54 is sufficient to locate the coiled section 54 within the urinary canal 36 at a position slightly proximal of the urinary sphincter muscle 34, as shown in FIGS. 6-9.

Located slightly proximally of the urinary sphincter muscle 34, the coiled section 54 of the inflation tube 44 functions as an anchor to assist in holding the indwelling catheter 20 in the urinary tract 26 in the position shown in FIG. 9. The coiled section 54 prevents the indwelling catheter 20 from moving distally from the position shown in FIG. 9, as a result of the coils of the coiled section 54 contacting a constriction in the urinary tract caused by constriction of the sphincter muscle 34. The coiled section 54 contacts the constriction to resist the distal movement of the indwelling catheter 20 and prevent it from moving into the bladder 32. The inflated balloon 40 creates a restriction at the distal end 38 of the indwelling catheter 20 to prevent it from moving proximally along the urinary canal 36 and out of the urinary tract 26. With the inflated balloon 40 located at the distal end of the indwelling catheter 20 and the anchoring coiled section 54 located on the proximal side of the sphincter muscle 34, the indwelling catheter 20 resists movement either into or out of the bladder 32 and into and out of the prostatic urethra. Instead, the indwelling catheter 20 is maintained in the use position.

With the indwelling catheter 20 in the use position anchored by the balloon 40 and the coiled section 54, urine or other fluid from the bladder 32 is able to flow through a passageway 56 (FIG. 3) in the indwelling catheter 20 and out of the proximal end of the catheter 20 past the dilated urinary sphincter muscle 34 (FIG. 9). The urinary sphincter muscle 34 retains the capability to constrict or close around the inflation tube 44 to stop the urine flow under normal human control. The urine is discharged into the urinary canal 36 in the normal manner. The final indwelling position of the catheter 20 permits normal control by the urinary sphincter muscle 34 over urine flow.

More details concerning the structure of the indwelling catheter 20 are illustrated in FIGS. 1-5. The indwelling catheter 20 includes a main or central body 58, preferably made from silicone rubber, that has a generally cylindrical exterior shape. The main body 58 includes a sidewall 60 which defines the passageway 56 through the main body 58. An end piece 62 is either attached to or integral with the main body 58 at the distal end 38 of the catheter 20. The end piece 62 has a typical rounded tip configuration adapted to facilitate insertion of the catheter 20 and the insertion tool 22 into the urinary tract 26. At least one and preferably a pair of openings 64 are formed through the end piece 62. The openings 64 communicate between the exterior of the end piece 62 and the passageway 56 of the main body 58. Urine from the bladder 32 flows through the openings 64 and into and through the passageway 56 to the other end of the main body 58.

The balloon 40 is formed by a flexible sleeve 66 of relatively thin, flexible, expandable, usually-transparent and non-porous material which is attached with fluid-tight seals 68 and 70 around the exterior of the main body 36. A first fluid-tight seal 68 is located slightly proximally of the distal end of the main body 58 where the end piece 62 is attached, and a second fluid-tight seal 70 is spaced proximally along the main body 58 from the first seal 68 by a distance approximately equal to the axial length of the flexible sleeve 66. The fluid-tight seals 68 and 70 are preferably formed by attaching the flexible sleeve 66 to the main body 58 with an adhesive or by thermal welding.

The flexible sleeve 66 is positioned over the top of and extends axially on opposite sides of an opening 72 from the main body 58. The fluid-tight seals 68 and 70 are located distally and proximally of the opening 72, respectively. Fluid is introduced into a volume 74 at the exterior of the main body 58 between the fluid-tight seals 68 and 70 and within the flexible sleeve 66, causing the flexible sleeve 66 to expand outward and create the balloon 40.

Figure 3:
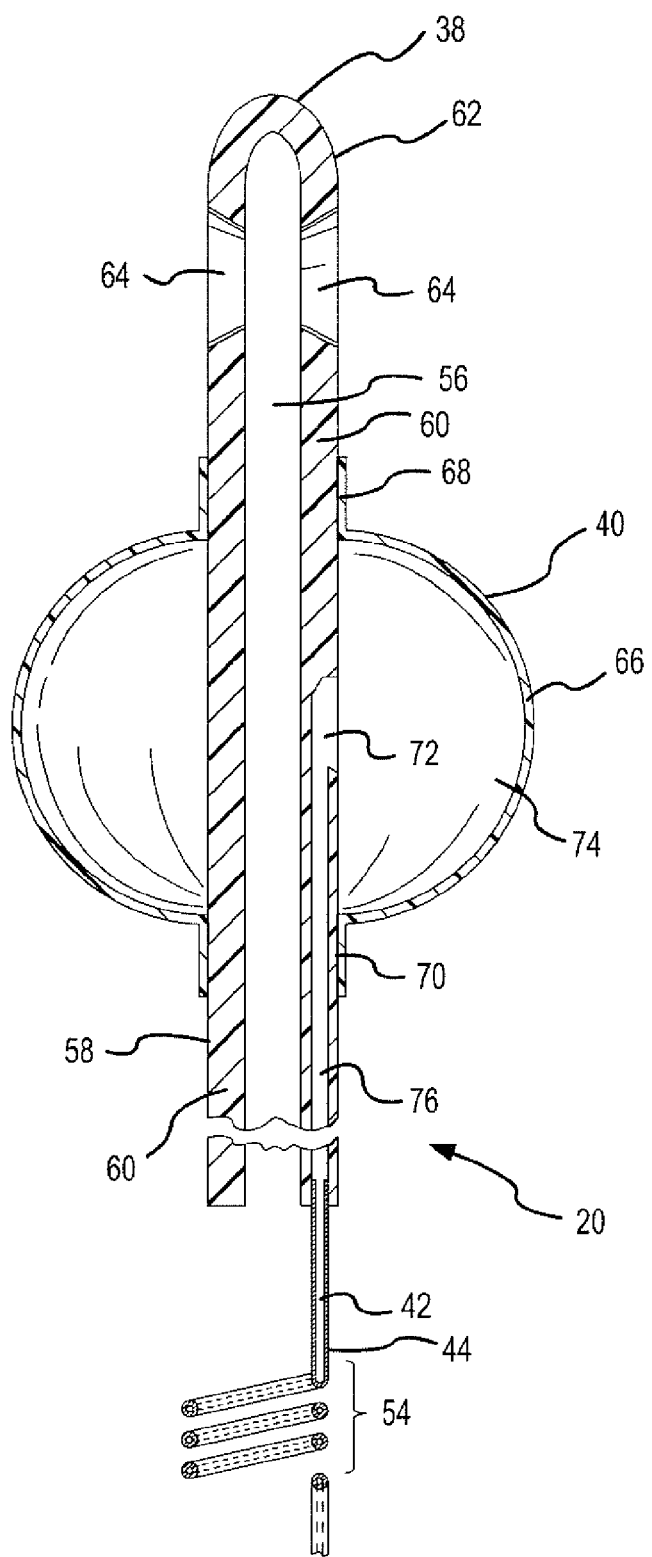
FIG. 3 is an enlarged longitudinal cross section view taken substantially in a longitudinal axial plane through FIG. 2.
Figure 5:
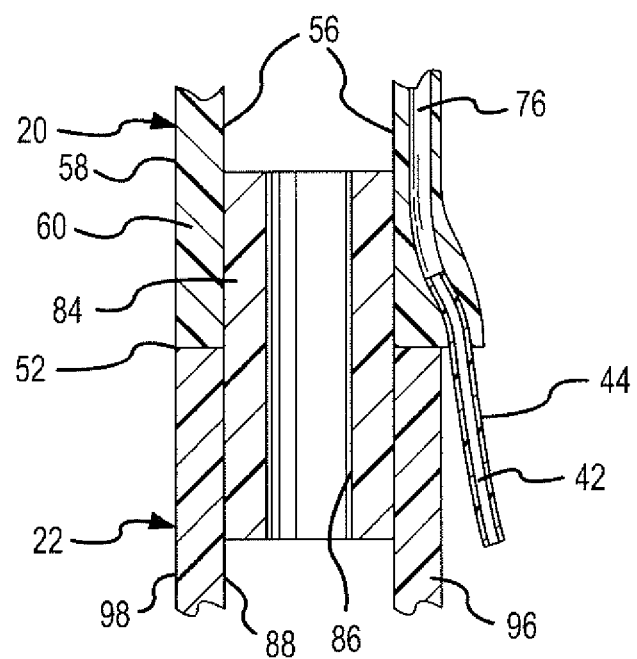
FIG. 5 is an enlarged partial longitudinal axial cross section view of a separable connection of the indwelling catheter-insertion tool assembly shown in FIG. 1, taken substantially in the plane of line 5-5 shown of FIG. 1.

An inflation conduit 76 communicates with the opening 72, as shown in FIG. 3. The inflation conduit 76 is formed within the sidewall 60 of the main body 58. A distal end of the inflation tube 44 is inserted into a proximal end of the inflation conduit 76, as shown in FIGS. 3 and 5. The fluid delivered from the syringe 48 (FIG. 1) into the inflation passageway 42 of the inflation tube 44 flows into the inflation conduit 76, out of the opening 72 and into the volume 74 beneath the flexible sleeve 66, causing the flexible sleeve 66 to expand into the form of the balloon 40.

Inserting the distal end of the inflation tube 44 into the inflation conduit 76, as shown in FIG. 5, allows the inflation tube 44 to bypass or go around the separable connection 52 between the indwelling catheter 20 and the insertion tool 22. A strong fluid-tight bond is formed by attaching the inflation tube 44 into the inflation conduit 76 with an adhesive. The attachment maintains the inflation tube 44 connected to the main body so that pulling on the inflation tube from the exterior of the urinary canal 36 will remove the catheter 20 from the urinary tract 26 without the inflation tube 44 breaking away from the main body 58. In this regard the inflation tube 44 also serves as a tether for the catheter 20. The separable connection 52 shown in FIG. 5 permits the communication between the inflation passageway 42 and the inflation conduit 76 to remain intact and fluid tight after the insertion tool 22 has separated from the indwelling catheter 20 while the catheter 20 remains positioned within the urinary tract. The continued integrity of the inflation passageway between the balloon 40 and the valve assembly 50 allows the balloon 40 to be periodically reinflated while the indwelling catheter 20 is in use, if necessary. Periodic reinflation may be necessary as a result of minute leaks in the balloon 40, the valve assembly 50 or the passageways connecting the balloon 40 and the valve assembly 50.

The inflation tube 44 has a length which extends from the indwelling catheter 20 through the urinary canal 36 to the outside of the human body. The length of the inflation tube 44 is sufficient to position the valve assembly 50 at the exterior of the human body. The inflation tube 44 has sufficient rigidity to prevent the inflation passageway 42 within the tube 44 from collapsing from contact with the tissue of the urinary tract 26, but the rigidity is not so great as to prevent a moderate amount of flexibility in the inflation tube 44. The moderate flexibility of the inflation tube 44 allows it to extend through the typical curves of the urinary tract 26.

The valve assembly 50 is of a conventional construction and includes a receptacle 78 into which a nozzle 80 of the syringe 48 is inserted, as shown in FIG. 1. The valve assembly 50 also includes a conventional internal check valve (not shown) which closes the inflation passageway 42 at the valve assembly 50 when the nozzle 80 is removed from the receptacle 78. In this manner, fluid from within the balloon 40 is prevented from escaping through the inflation passageway 42 when the syringe 48 is disconnected from the valve assembly 50, but the check valve permits fluid from the syringe 48 to inflate the balloon 40 when a plunger (not specifically shown) of the syringe 48 is depressed. Thus, the balloon 40 will remain inflated after the syringe 48 is disconnected from the valve assembly 50. However, should the balloon 40 need to be reinflated or should additional fluid need to be added to expand the balloon 40 during use of the catheter, the syringe 48 is easily connected to the valve assembly 50 for doing so.

As an alternative to the use of the valve assembly 50, the inflation passageway 42 can be sealed at a proximal end after the balloon 40 has been inflated. For example, instead of using the valve assembly 50 to prevent fluid from escaping from the balloon, a knot (not shown) may be formed or tied in the proximal end of the inflation tube 44 at a location spaced proximally from the end of the penis. The knot seals the inflation passageway 42 and prevents the fluid from escaping through the passageway to maintain the balloon 40 inflated. The inflation tube 42 is cut at a position slightly proximally of the knot. In this alternative configuration, the inflation tube 44 without the valve assembly 50 extends only a modest distance from the end of the urinary canal 36. Greater comfort and convenience is promoted because there is no sizable apparatus to deal with, such as the valve assembly 50 connected to the proximal end of the inflation tube 44. If the balloon 40 needs to be reinflated or have additional fluid added after the indwelling catheter 20 has been used for some time, the knot can be cut from the end of the inflation tube 44 and a suitable connector attached to allow the syringe 48 to introduce additional fluid. After suitable inflation, another knot can be tied in the remaining proximal portion of the inflation tube 40. Releasing the fluid through the inflation passageway 42 collapses the balloon 40 and allows the catheter 20 to be pulled out of the urinary canal 36 by pulling on the inflation tube 44.

The insertion tool 22 is a flexible tubular structure and is generally configured similar to the distal portion of a typical urinary catheter. The insertion tool 22 is at least long enough to extend from outside of the body into the urinary canal 36 and prostatic urethra 28 to a point that will place the indwelling catheter 20 in the final desired use position. The insertion tool 22 is preferably made from silicone rubber, but has sufficient structural integrity to transfer pushing forces supplied on the outside of the body longitudinally along the length of the insertion tool 22, thereby allowing the insertion tool 22 with the attached indwelling catheter 20 to be moved distally into the urinary tract 26. A proximal end of the insertion tool 22 may take the form of a hollow handle 82 or enlargement, by which to grip the insertion tool 22 and apply pushing force to it during insertion in the urinary tract 26.

The separable connection 52 between the insertion tool 22 and the indwelling catheter 20 includes a sleeve 84, shown in FIG. 5. The sleeve 84 is rigidly connected to the distal end of the insertion tool 22 by an adhesive, for example. A distal portion of the sleeve 84 projects beyond the distal end of the insertion tool 22. The distal portion of the sleeve 84 has an exterior diameter which frictionally fits within the interior passageway 56 of the indwelling catheter 20. The friction created by the insertion of the sleeve 84 into the interior passageway 56 is sufficient to retain the indwelling catheter 20 to the insertion tool 22 during manipulation of the catheter-tool assembly 24 within the urinary tract 26 during insertion and placement, prior to inflation of the balloon 40. However, the degree of frictional resistance between the distal end of the sleeve 84 and the interior passageway 56 is not so great as to prevent the indwelling catheter 20 from separating from the insertion tool 22 once the balloon 40 has been inflated and seated against the bladder neck 46. The amount of frictional resistance between the distal portion of the sleeve 84 and the proximal end of the main body 58 at the proximal end of the interior passageway 56 can be increased by forming serrations on the an exterior of the distal end of the sleeve 84. The resilient material of the main body 58 will deform slightly around the serrations to further assistant holding the indwelling catheter 20 to the insertion tool 22, but the amount of deformation is not so great as to prevent separation of the indwelling catheter 20 and the insertion tool 22 at the separable connection 52. The sleeve 84 has a center opening 86 formed through it to provide a fluid flow path from the passageway 56 through the sleeve 84.

The catheter-tool assembly 24 is inserted and used in the manner illustrated in FIGS. 6-9. As shown in FIG. 6, the catheter 20 and the insertion tool 22 are inserted into the urinary tract 26 through the urinary canal 36, in a manner similar to the way that a conventional full length urinary catheter would be inserted. The insertion force is applied by pushing on the insertion tool 22 and on the handle 82 attached at its proximal end. Distal movement of the catheter-tool assembly 24 continues until the rounded end 62 and a significant distal portion of the indwelling catheter 20 are located in the bladder 32. The insertion is sufficient to assure that the flexible sleeve 66 will be located within the bladder 32. To assure sufficient insertion, it is frequently the case that the distal movement continues until terminated when the end 38 contacts the opposite side of the bladder 32 wall, thereby assuring that the balloon 40 is within the bladder 32. During insertion in this manner, the coiled section 54, which is wrapped around the insertion tool 22, helps keep the forward portion of the inflation tube 44 aligned and progressing with the indwelling catheter 20.

Once the catheter-tool assembly 24 has been inserted sufficiently, the balloon 40 is inflated as shown in FIG. 7. Inflation is achieved by connecting the syringe 48 to the valve assembly 50, and depressing the plunger (not shown) of the syringe 48 to force fluid through the inflation passageway 42 of the inflation tube 44, into the inflation conduit 76, through the opening 72 and into the interior volume 74, causing the flexible sleeve 66 to expand into the balloon 40. After the balloon 40 is in the expanded position, the insertion tool 22 is pulled to move the catheter-tool assembly 24 in the proximal direction until the inflated balloon 40 seats against the bladder neck 46.

With the balloon 40 seated against the bladder neck 46, continued proximal movement of the insertion tool 22 causes the separable connection 52 to separate the indwelling catheter 20 from the insertion tool 22, as shown in FIG. 8. The balloon 40 prevents the indwelling catheter 20 from coming out of the urinary tract 26 with the insertion tool 22 because the expanded balloon 40 is larger than the bladder neck 46. The coiled section 54 of the inflation tube 44, being located proximally from the urinary sphincter muscle 34, prevents the indwelling catheter 20 from moving into the bladder 32. The continued withdrawal of the insertion tool 22 is not inhibited by the coiled section 54, because the body of the insertion tool 22 moves through the interior of the coiled section 54. The length of the inflation tube 44 is sufficient to locate the valve assembly 50 at the exterior of the urinary tract 26.

After the insertion tool 22 is removed as shown in FIG. 9, the balloon 40 remains inflated in the bladder 32, and the proximal end of the main body 58 of the indwelling catheter 20 extends through the prostatic urethra 28 but does not extend through the urinary sphincter muscle 34. The coiled section 54 is located on the opposite or proximal side of the urinary sphincter muscle 34. In this final position, the balloon 40 prevents the indwelling catheter 20 from moving out of the prostatic urethra 28 and into the urinary canal 36, while the coiled section 54 prevents the indwelling catheter 20 from moving out of the prostatic urethra 28 and into the bladder 32. The inflation tube 44 does not interfere with the ability of the urinary sphincter muscle 34 to constrict around the inflation tube 44 and naturally stop the urine flow. Similarly, the inflation tube 44 does not interfere with the natural ability of the urinary sphincter muscle 34 to dilate, as shown in FIG. 9, and thereby naturally allow urine to flow through the interior passageway 56 of the indwelling catheter 20 and into the urinary canal 36. In this manner, the inflation tube 44 does not interfere with the natural control functions of the urinary sphincter muscle 34.

When the urinary sphincter muscle 34 is dilated, the urine flows from the bladder 32 through the openings 64 and into the interior passageway 56 in the main body 58, as understood from FIG. 3. The flow of urine through the interior passageway 56 largely bypasses the prostatic urethra 28 or the prostate gland tissue if the prostatic urethra 28 has been removed by a surgical procedure. The dilated urinary sphincter muscle 34 (FIG. 9) allows urine to flow from the interior passageway 56 of the indwelling catheter 20 through the urinary canal 36 in the normal manner. Constriction of the urinary sphincter muscle 34 around the inflation tube 44 stops the urine flow.

While the urinary sphincter muscle 34 is dilated to permit urine flow, the balloon 40 prevents the indwelling catheter 20 from exiting the bladder 32 and moving into the dilated urinary sphincter muscle 34. The contact of the coiled section 54 against the urethra resists movement of the indwelling catheter 20 into and out of the bladder 32. In addition, the inflation tube 44 can be held at the valve assembly 50 to resist distal movement of the indwelling catheter 20 during urination when the urinary sphincter muscle 34 is dilated, if necessary or desirable. In this manner, the indwelling catheter 20 stays in position even when the urinary sphincter muscle 34 is dilated.

When the indwelling catheter 20 is no longer needed, typically as a result of natural healing of the prostate gland 30 after a surgical procedure, or if it is necessary to periodically replace the indwelling catheter 20, removal is accomplished after deflating the balloon 40. Deflation is accomplished by inserting the syringe 48 into the valve assembly 50 and moving the plunger (not shown) of the syringe 48 outward to withdraw fluid from the inflation passageway 42. The insertion of the syringe 48 in the valve assembly 50 opens the check valve within the valve assembly 50 and allows the fluid to be withdrawn. If the inflation tube 44 has been tied into a knot to avoid use of the valve assembly 50 in the manner described above, the inflation tube 44 may be cut at a location distal of the knot to allow the fluid to escape. The escaping fluid causes the balloon 40 to deflate, and the flexible sleeve 66 moves to a collapsed position (shown in FIGS. 1 and 6) adjacent to the main body 58 of the indwelling catheter 20.

Once the balloon 40 has been deflated, the inflation tube 44 is pulled outward by gripping and pulling on the valve assembly 50 or the proximal end of the inflation tube 44. Force is transferred through the inflation tube 44 to the indwelling catheter 20. The pulling force constricts and elongates the coils of the coiled section thereby reducing their transverse dimension as a result of longitudinally separating the individual coils with the pulling force. The reduced transverse dimension lessens or eliminates contact with the urinary canal 36. In this manner the coiled section does not inhibit removal of the catheter or induce significant discomfort as it moves through the urinary canal. The amount of force transferred is sufficient to move the indwelling catheter 20 past the urinary sphincter muscle 34 and into the urinary canal 36. The deflated balloon 40 does not resist movement of the distal end of the indwelling catheter 20 through the bladder neck 46. Continued pulling movement on the inflation tube 44 moves the indwelling catheter 20 through the urinary canal 36 until the indwelling catheter 20 is completely withdrawn from the proximal end of the urinary canal 36.

In many microwave thermotherapy and transurethral resection of the prostate (TURP) procedures, blood from the affected tissue tends to accumulate in the bladder. The constricted urinary sphincter muscle 34 prevents the blood from flowing out of the urinary canal 26, accept during natural urination. With the indwelling catheter 20 located in the use position described above, the blood may clot within the interior passageway 56 of the indwelling catheter 20. The blood clots may accumulate to the degree that the interior passageway 56 becomes blocked or obstructed. Natural pressure from the bladder may be insufficient to overcome the blockage, thereby preventing urine flow from the bladder. Under such circumstances, it is necessary to remove the obstructed indwelling catheter 20 insert a new unobstructed indwelling catheter 20, in the manner described above. Replacing the indwelling catheter to overcome blockage from blood clots is to be avoided if possible, because the removal and insertion further aggravates the already-tender tissue within the prostate gland that has been affected by the procedure.

One approach which avoids replacing the indwelling catheter under circumstances where blood clots accumulate in the interior passageway 56 is to flush the interior passageway 56 with saline or other appropriate liquid on a periodic basis. To do so, it is necessary to establish fluid communication through the canal, the constricted sphincter muscle and into the interior passageway 56 of the indwelling catheter 20. The most direct manner of establishing fluid communication in this manner is to maintain the insertion tool 22 connected to the indwelling catheter 20, so that the flushing fluid can be supplied through an interior channel 88 of the insertion tool 22 from the handle 82, as understood from FIG. 10. The flushing fluid passes through the interior channel 88 and through the center opening 86 of the sleeve 84 and into the passageway 56 of the indwelling catheter 20. The flushing fluid forces any blood clots which accumulated in the interior passageway 56 back into the bladder 32 (FIG. 6) or dissolves the clots within the interior passageway 56. Removing the clots relieves the obstruction and allows urine to flow through the indwelling catheter in the manner described.

Until the affected tissue stops bleeding, there is a risk that the clots will continue to form within the passageway 56. The risks of obstruction from blood clots is normally the greatest within the first twenty-four hours after the microwave thermotherapy, TURP or other surgical procedure. During this time period, it is desirable to provide the ability to flush the interior passageway 56. To provide the ability to flush the interior passageway 56, the insertion tool 22 must remain connected to the indwelling catheter 20 during this time so that the interior channel 88 of the insertion tool 22 remains in fluid communication with the interior passageway 56, through the center opening 86 of the sleeve 84.

Instead of pulling the insertion tool 22 in the proximal direction to separate the insertion tool 22 from the indwelling catheter 20 at the separable connection 52 after the indwelling catheter has been located in the use position (FIG. 8), the insertion tool may be left in place for approximately the first twenty-four hours. The natural friction between the proximal end of the main body 58 of the indwelling catheter 20 and the distal portion of the sleeve 84 connected to the insertion tool 22 may be sufficient to maintain the insertion tool 22 connected to the indwelling catheter in some circumstances. However in other circumstances, the patient may be released from the supervision of medical personnel immediately after the procedure and will be ambulatory during the first twenty-four hour period after the procedure. Movement of the patient under these circumstances may tend create sufficient forces on the insertion tool 22 to disconnect the insertion tool from the indwelling catheter prematurely before the risk of blood clots has subsided.

Figure 10:
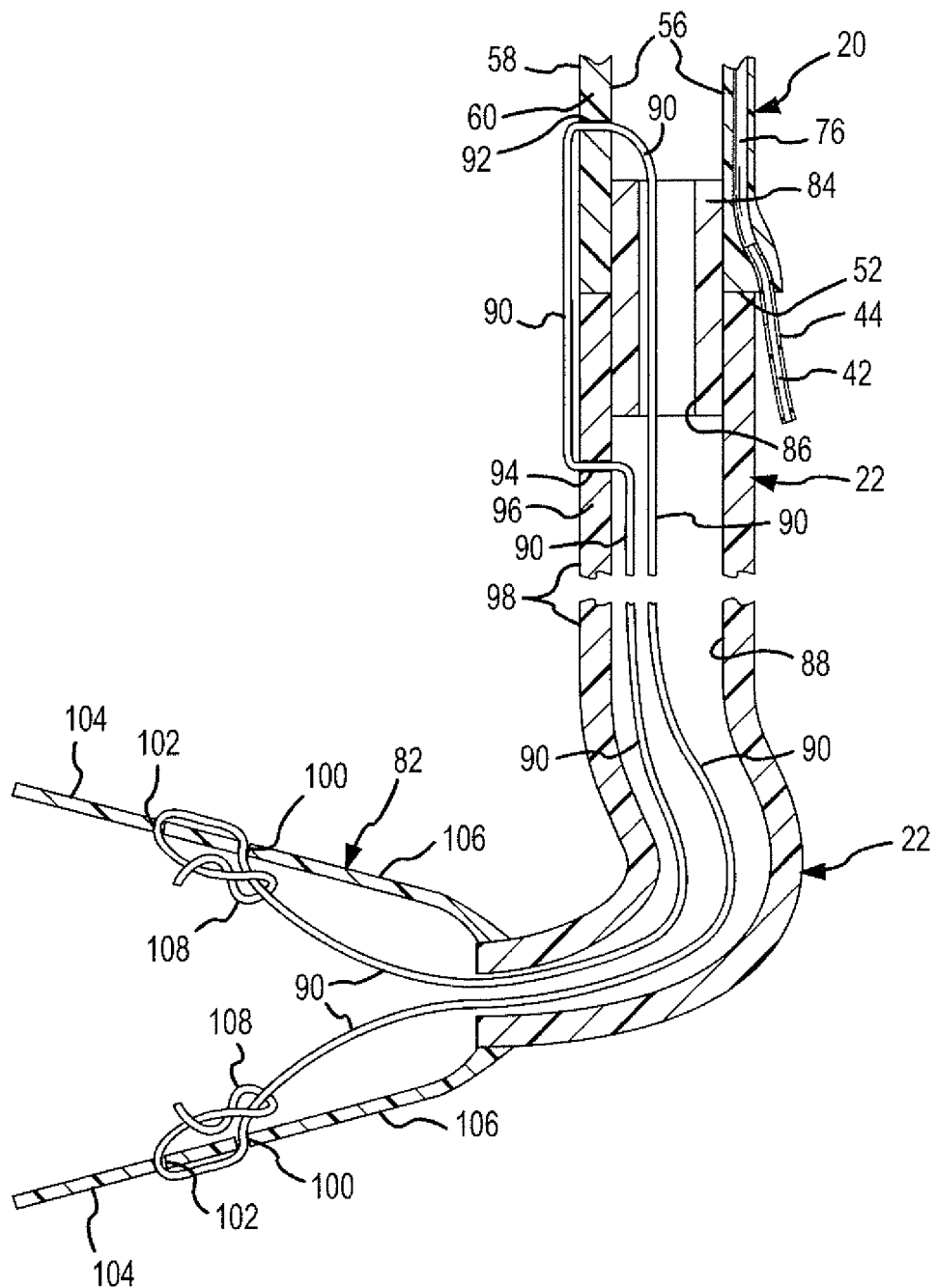
FIG. 10 is a partial, enlarged and broken view of the catheter-insertion tool assembly shown in FIG. 1, illustrating an alternative embodiment of the separable connection shown in FIG. 5, and other aspects of the invention.

To assure that the insertion tool 22 remains connected to the indwelling catheter 20 at the separable connection 52 until medical personnel determines that it is appropriate to separate the indwelling catheter 20 from the insertion tool 22, a bridging structure, preferably in the form of a relatively fine thread-like cord 90, is used to maintain temporarily the separable connection 52 of the indwelling catheter 20 and the insertion tool 22, as shown in FIG. 10. The cord 90 extends from the interior passageway 56 through a small hole 92 in the sidewall 60 of the main body 58 of the indwelling catheter 20. From the hole 92, the cord 90 extends across and bridges the separable connection 52 along an outside surface of the main body 56 of the indwelling catheter and along an outside surface of a tubular main body 98 of the insertion tool 22. The cord also extends through another small hole 94 in a sidewall 96 of a main tubular body 98 of the insertion tool 22, and into the interior channel 88. The two opposite free-end portions of the cord 90 extend along the length of the interior channel 88 and terminate within the hollow interior of the handle 82. The terminal end portions of the cord 90 each loop through small holes 100 and 102 formed in a sidewall 104 of a main body 106 of the handle 82. Knots 108 are formed in the terminal end portions of the cord 90 within the hollow interior of the handle 82 to hold each end of the cord 90 in place relative to the handle 82.

Any slack longitudinal length of the cord 90 is eliminated when the knots 108 are tied in the terminal ends of the cord 90. Eliminating any longitudinal slack in the cord 90 pulls together the proximal end of the indwelling catheter 20 and the distal end of the insertion tool 22. The cord 90 therefore prevents the indwelling catheter 20 from separating from the insertion tool 22 at the separable connection 52. The communication channel through the interior channel 88, the center opening 86 of the sleeve 84 and the interior passageway 56 is maintained so long as the cord 90 connects the indwelling catheter 20 and the insertion tool 22.

While the indwelling catheter 20 is maintained connected to the insertion tool 22, flushing fluid may be forced from the handle 82 through the interior channel 88, through the center opening 26 and into the interior passageway 56. The flushing fluid dissolves any clots within the interior passageway 56, and keeps that passageway 56 unobstructed for urine flow from the bladder. The dissolved clots may flow from the interior passageway 56 through the interior channel 88, or the clots may be pushed back into the bladder with the flushing fluid. Of course, while the open communication path exists through the insertion tool 22 and the indwelling catheter 20, urine from the bladder will also flow through this open path. To control the urine flow under the circumstances, it is necessary to insert a valve in the interior channel 88 at the handle 82, to control the discharge of the urine. The extension of the insertion tool 22 through the sphincter muscle 34 prevents the sphincter muscle from naturally controlling the urine flow.

When it is determined that the risk of blood clots has diminished and it is no longer necessary or desirable to flush the interior passageway 56 of the indwelling catheter 20, preferably at least twenty-four hours after the procedure, one or both of the knots 108 is untied or cut. One end of the cord 90 is pulled in the proximal direction, which moves the other free end of the cord is moved into the interior channel 88, through the holes 92 and 94 and then out of the interior channel 88, thereby disconnecting the indwelling catheter 20 from the insertion tool 22 at the separable connection 50. Once the cord 90 no longer holds the indwelling catheter and the insertion tool together as shown in FIG. 10, the insertion tool 22 is pulled in the proximal direction to separate it from the indwelling catheter 20 in the manner previously described and shown in FIG. 8. The indwelling catheter 20 remains in the use position shown in FIG. 9 where its use secures numerous advantages and improvements.

In the manner described, the indwelling catheter 20 allows continued natural use of the urinary sphincter muscle 34 in the normal manner to start and stop urine flow. The location of the indwelling catheter 20 within the prostate gland 30 bypasses most of the urine flow from the tissue of the prostate gland 30 which has been affected by the surgical procedure, thereby preventing or lessening pain and irritation. Any blood which may accumulate within the interior passageway of the indwelling catheter 20, and possibly cause obstructions due to clots, is flushed from the interior of the indwelling catheter prior to removal of the insertion tool 22. The separation of the insertion tool 22 from the indwelling catheter 20 may be delayed until the risks of obstructions from blood clots and the like has passed. The indwelling catheter 20 also assures a passageway for urine to flow through a prostate gland 30 that is diseased and swollen from BPH, while preserving natural control over the urine flow in the normal manner by the urinary sphincter muscle. The indwelling catheter 20 reliably remains in position for use due to the anchoring effects of the inflated balloon 40 and the coiled section 54, thereby lessening the risk of further procedures to reposition and remove an indwelling catheter that has inadvertently moved. Many other advantages and improvements will be apparent upon gaining a full knowledge and appreciation of the present invention.

A presently preferred embodiment of the present invention and many of its improvements have been described with a degree of particularity. This description is a preferred example of implementing the invention, and is not necessarily intended to limit the scope of the invention. The scope of the invention is defined by the following claims.

What is claimed:

1. A method of draining urine from a bladder to a position distal of a urinary sphincter muscle in a urinary tract which also includes a urinary canal extending from the sphincter muscle to an exterior opening, comprising:
    positioning an indwelling catheter having an inflatable balloon in the urinary tract in a use position in which the indwelling catheter extends from the bladder to a position distally adjacent to the sphincter muscle;
    extending an inflation tube having a coiled section within the urinary tract from the indwelling catheter through the portion of the urinary canal surrounded by the sphincter muscle and out of the exterior opening;
    inflating the balloon within the bladder by delivering fluid though the inflation tube and into the balloon;
    retaining the indwelling catheter against proximal movement from the use position by contacting the inflated balloon with the bladder;
    retaining the indwelling catheter against distal movement from the use position by contacting the coiled section with a constriction of the urinary tract caused by the sphincter muscle at a location proximally adjacent to the constriction; and
    draining urine through the indwelling catheter from the bladder to a position in the urinary tract distally adjacent to the sphincter muscle.

2. A method as defined in claim 1, further comprising:
    withdrawing the indwelling catheter from the urinary tract by moving the inflation tube proximally at the exterior opening.

3. A method as defined in claim 2, further comprising:
    resiliently deflecting the coiled section to a lesser transverse dimension while moving the inflation tube proximally when withdrawing the indwelling catheter.

4. A method as defined in claim 1, further comprising:
    attaching the indwelling catheter to an insertion tool;
    inserting the indwelling catheter into the urinary tract from the exterior opening while the indwelling catheter is connected to the insertion tool;
    manipulating the insertion tool to position the indwelling catheter in the use position;
    detaching the insertion tool from the indwelling catheter after the indwelling catheter has been positioned in the use position; and
    withdrawing the insertion tool from the urinary tract after detaching the insertion tool from the indwelling catheter.

5. A method as defined in claim 4, further comprising:
    extending the insertion tool through the coiled section of the inflation tube while the indwelling catheter is attached to the insertion tool.

6. A method as defined in claim 4, further comprising:
    attaching the indwelling catheter to the insertion tool by connecting a selectively disconnectable bridging structure between the indwelling catheter and the insertion tool;
    detaching the catheter from the insertion tool by disconnecting the bridging structure to permit separating the indwelling catheter from the insertion tool.

7. A method as defined in claim 6, further comprising:
    using a cord which includes one portion which extends between the indwelling catheter and the insertion tool as the bridging structure and which includes another portion which is adapted to extend within the urinary canal along the insertion tool through the exterior opening; and
    eliminating the extension of the cord between the indwelling catheter and the insertion tool when disconnecting the bridging structure by distally moving the cord at a location distal of the exterior opening.

8. A method as defined in claim 7, wherein the insertion tool defines an interior channel which extends between opposite ends of the insertion tool, and the indwelling catheter defines an interior passageway which extends from the bladder to the position distally adjacent to the sphincter muscle when the indwelling catheter is in the use position; and further comprising:
    establishing a fluid communication path between the interior channel of the insertion tool and into the interior passageway of the indwelling catheter when the insertion tool is attached to the indwelling catheter.

9. A method as defined in claim 8, further comprising:
    extending the cord through the interior channel of the insertion tool when the bridging structure connects the indwelling catheter to the insertion tool.

10. A method as defined in claim 4, wherein the insertion tool defines an interior channel which extends between opposite ends of the insertion tool, and the indwelling catheter defines an interior passageway which extends from the bladder to the position distally adjacent to the sphincter muscle when the indwelling catheter is in the use position; and further comprising:
    establishing a fluid communication path between the interior channel of the insertion tool and into the interior passageway of the indwelling catheter when the insertion tool is attached to the indwelling catheter; and
    communicating flushing fluid through the interior channel of the insertion tool and into the interior passageway of the indwelling catheter.

11. A method as defined in claim 10, further comprising:
    supplying flushing fluid into the interior channel of the insertion tool at an end of the insertion tool adapted to be located proximal of the exterior opening to deliver the flushing fluid into the interior passageway of the indwelling catheter.

12. A method of using an indwelling catheter and an insertion tool to drain urine in a urinary tract which includes a urinary canal that extends from a bladder to an exterior opening with a urinary sphincter muscle which surrounds the urinary canal at a position between the bladder and the exterior opening, the indwelling catheter defining an interior passageway and the insertion tool including an interior channel, comprising:
    attaching the indwelling catheter to the insertion tool at a separable connection;
    temporarily inseparably connecting the indwelling catheter and the insertion tool at the separable connection to maintain the attachment of the indwelling catheter to the insertion tool at the separable connection;

inserting the indwelling catheter into the urinary tract from the exterior opening while the indwelling catheter is temporarily inseparably connected to the insertion tool;

manipulating the insertion tool to position the temporarily inseparably connected indwelling catheter in a use position in which a distal end of the indwelling catheter is located in the bladder and a proximal end of the indwelling catheter is located distally adjacent to the sphincter muscle;

including an inflatable balloon on the indwelling catheter;

extending an inflation tube within the urinary tract from the indwelling catheter through the portion of the urinary canal surrounded by the sphincter muscle and out of the exterior opening;

resisting proximal movement of the indwelling catheter from the use position by inflating the balloon within the bladder with inflation fluid delivered though the inflation tube;

including a coiled section in the inflation tube at a location adjacent to and proximal of the sphincter muscle when the indwelling catheter is located in the use position;

resisting distal movement of the indwelling catheter from the use position by contacting the coiled section with a constriction of the urinary tract caused by constriction of the sphincter muscle at a location proximal of the constriction;

inserting the insertion tool through the coiled section of the inflation tube before inserting the indwelling catheter into the urinary tract and before manipulating the insertion tool to position the temporarily inseparably connected indwelling catheter in the use position;

draining urine from the bladder through the exterior opening through an interior passageway in the indwelling catheter and an interior channel in the insertion tool while the indwelling catheter and the insertion tool are temporarily inseparably connected;

eliminating the temporary inseparable connection of the indwelling catheter and the insertion tool after the indwelling catheter has been located in the use position;

detaching the insertion tool from the indwelling catheter without disturbing the indwelling catheter from the use position after the temporary inseparable connection has been eliminated;

maintaining the insertion tool within the coiled section of the inflation tube until after the insertion tool is detached from the indwelling catheter; and withdrawing the insertion tool from the urinary tract after detaching the insertion tool from the indwelling catheter.

13. A method as defined in claim 12, further comprising:

extending a cord between the indwelling catheter and the insertion tool at the separable connection to bridge between the indwelling catheter and the insertion tool.

14. A method as defined in claim 13, further comprising:

eliminating the extension of the cord between the indwelling catheter and the insertion tool at the separable connection to eliminate the temporarily inseparable connection.

15. A method as defined in claim 14, further comprising:

extending an end of the cord from the separable connection through the interior channel of the insertion tool to a position outside of the exterior opening and outside of the interior channel of the insertion tool; and eliminating the extension of the cord between the indwelling catheter and the insertion tool at the separable connection by moving the end of the cord distally at the outside of the insertion tool.

16. A method as defined in claim 12, further comprising:

flushing the interior passageway of the indwelling catheter with flushing fluid supplied through the interior channel of the insertion tool before eliminating the temporary inseparable connection.

17. A method as defined in claim 12, further comprising:

removing the indwelling catheter from the use position by deflating the balloon and moving the inflation tube proximally from the exterior opening to pull the indwelling catheter through the urinary tract out of the exterior opening.

18. A method as defined in claim 12, further comprising:

inserting the indwelling catheter in the urinary tract after performing a surgical procedure on the prostate gland;

draining urine and blood from the prostate gland which accumulates in the bladder through an interior passageway of the indwelling catheter; and flushing the interior passageway of the indwelling catheter with flushing fluid supplied from the exterior opening through the urinary canal to the interior passageway to remove obstructions caused by blood clots within the interior passageway.

19. A method as defined in claim 12, further comprising:

flushing the interior passageway of the indwelling catheter with flushing fluid supplied through an interior channel of the insertion tool at the exterior opening.

* * * * *